US009119607B2

(12) United States Patent
Amin

(10) Patent No.: US 9,119,607 B2
(45) Date of Patent: Sep. 1, 2015

(54) HEART OCCLUSION DEVICES

(75) Inventor: Zahid Amin, Omaha, NE (US)

(73) Assignee: Gore Enterprise Holdings, Inc., Newark, DE (US)

(*) Notice: Subject to any disclaimer, the term of this patent is extended or adjusted under 35 U.S.C. 154(b) by 225 days.

(21) Appl. No.: 12/400,445

(22) Filed: Mar. 9, 2009

(65) Prior Publication Data

US 2009/0228038 A1 Sep. 10, 2009

Related U.S. Application Data

(60) Provisional application No. 61/034,772, filed on Mar. 7, 2008.

(51) Int. Cl.
| A61B 17/08 | (2006.01) |
| A61B 17/00 | (2006.01) |
| A61B 17/12 | (2006.01) |

(52) U.S. Cl.
CPC ....... *A61B 17/0057* (2013.01); *A61B 17/12022* (2013.01); *A61B 17/12122* (2013.01); *A61B 17/12145* (2013.01); *A61B 17/12172* (2013.01);
(Continued)

(58) Field of Classification Search
CPC ................. A61B 17/0057; A61B 2017/00575; A61B 17/08; A61B 17/12022; A61B 17/12122; A61B 17/12145; A61B 17/1214
USPC ......................................................... 606/213
See application file for complete search history.

(56) References Cited

U.S. PATENT DOCUMENTS 5,976,174 A 11/1999 Ruiz
6,024,756 A 2/2000 Huebsch et al.
(Continued)

FOREIGN PATENT DOCUMENTS

| DE | 102006036649 | 10/2007 |
| EP | 2340770 | 7/2011 |

(Continued)

OTHER PUBLICATIONS

International Search Report and Written Opinion for PCT/US2014/017129 mailed May 14, 2014, 9 pages.
(Continued)

*Primary Examiner* — Gregory Anderson
*Assistant Examiner* — Son Dang
(74) *Attorney, Agent, or Firm* — Fish & Richardson P.C.

(57) ABSTRACT

The present invention is specifically directed to a heart occlusion device with a self-centering mechanism. The heart occlusion device includes two separate uniquely shaped wires 12, 14, each forming shapes that mirror the respective wire's shapes. Each wire forms half-discs or quarter-discs that together form a distal disc and a proximal disc. In other versions, the device includes four separate wires, each mirroring its neighboring wire and forming a proximal and a distal quarter-disc. In the versions with four wires, the quarter-discs of each wire together form proximal and distal discs. The distal disc and proximal disc are separated by a self-centering waist. The proximal disc is attached to a hub comprising a screw mechanism. A similar hub is optional on the distal disc. The discs further include coverings which form a sealant to occlude an aperture in a tissue. The wires forming the discs have a shape-memory capability such that they can be collapsed and distorted in a catheter during delivery but resume and maintain their intended shape after delivery.

23 Claims, 11 Drawing Sheets

(52) U.S. Cl.
CPC .............. *A61B 2017/00243* (2013.01); *A61B 2017/00557* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00632* (2013.01); *A61B 2017/00867* (2013.01); *A61B 2017/12095* (2013.01)

(56) References Cited

U.S. PATENT DOCUMENTS

| | | |
|---|---|---|
| 6,214,029 B1 | 4/2001 | Thill et al. |
| 6,270,515 B1 | 8/2001 | Linden |
| 6,355,052 B1 | 3/2002 | Neuss |
| 6,375,671 B1 | 4/2002 | Kobayashi |
| 6,554,849 B1 | 4/2003 | Jones et al. |
| 7,207,402 B2 | 4/2007 | Bjoerk |
| 7,335,426 B2 | 2/2008 | Marton et al. |
| 7,658,748 B2 | 2/2010 | Marino et al. |
| 7,842,053 B2 | 11/2010 | Chanduszko et al. |
| 7,871,419 B2 * | 1/2011 | Devellian et al. .......... 606/157 |
| 7,887,562 B2 | 2/2011 | Young et al. |
| 8,308,760 B2 | 11/2012 | Chanduszko |
| 8,753,362 B2 | 6/2014 | Widomski et al. |
| 8,821,528 B2 | 9/2014 | McGuckin et al. |
| 8,858,576 B2 | 10/2014 | Takahashi et al. |
| 2002/0111647 A1 | 8/2002 | Khairkhahan et al. |
| 2003/0130683 A1 | 7/2003 | Andreas et al. |
| 2003/0171774 A1 | 9/2003 | Freudenthal et al. |
| 2003/0191495 A1 | 10/2003 | Ryan et al. |
| 2003/0225421 A1 | 12/2003 | Peavey |
| 2003/0225439 A1 | 12/2003 | Cook et al. |
| 2004/0073242 A1 * | 4/2004 | Chanduszko .............. 606/157 |
| 2004/0133230 A1 | 7/2004 | Carpenter et al. |
| 2004/0176799 A1 * | 9/2004 | Chanduszko et al. ........ 606/213 |
| 2004/0254594 A1 | 12/2004 | Alfaro |
| 2005/0043759 A1 | 2/2005 | Chanduszko |
| 2005/0187564 A1 | 8/2005 | Jayaraman |
| 2005/0187568 A1 | 8/2005 | Klenk et al. |
| 2005/0192626 A1 | 9/2005 | Widomski et al. |
| 2005/0267525 A1 | 12/2005 | Chanduszko |
| 2005/0288706 A1 | 12/2005 | Widomski et al. |
| 2005/0288786 A1 | 12/2005 | Chanduszko |
| 2006/0025790 A1 | 2/2006 | de Winter et al. |
| 2006/0116710 A1 | 6/2006 | Corcoran et al. |
| 2006/0122647 A1 * | 6/2006 | Callaghan et al. .......... 606/213 |
| 2006/0167494 A1 | 7/2006 | Suddaby |
| 2007/0265656 A1 | 11/2007 | Amplatz et al. |
| 2008/0065149 A1 | 3/2008 | Thielen et al. |
| 2008/0208214 A1 | 8/2008 | Sato et al. |
| 2008/0228218 A1 | 9/2008 | Chanduszko |
| 2009/0062844 A1 | 3/2009 | Tekulve |
| 2009/0204133 A1 | 8/2009 | Melzer et al. |
| 2009/0292310 A1 | 11/2009 | Chin et al. |
| 2010/0234885 A1 | 9/2010 | Frazier et al. |
| 2011/0054519 A1 | 3/2011 | Neuss |
| 2012/0071918 A1 | 3/2012 | Amin et al. |
| 2012/0245623 A1 | 9/2012 | Kariniemi et al. |
| 2012/0316597 A1 | 12/2012 | Fitz et al. |
| 2013/0165967 A1 | 6/2013 | Amin et al. |

FOREIGN PATENT DOCUMENTS

| | | |
|---|---|---|
| JP | 2000505668 A | 5/2000 |
| JP | 2000300571 A | 10/2000 |
| JP | 2005521447 A | 7/2005 |
| JP | 2005521818 A | 7/2005 |
| JP | 2005534390 A | 11/2005 |
| JP | 2006230800 A | 9/2006 |
| SU | 1377052 A1 | 2/1988 |
| WO | 03/103476 | 12/2003 |
| WO | WO2004012603 A3 | 5/2004 |
| WO | WO 2008153872 | 12/2008 |
| WO | WO2007124862 A8 | 1/2009 |

OTHER PUBLICATIONS

International Preliminary Report on Patentability and Written Opinion for PCT/US2009/004307, mailed Sep. 13, 2011, 8 pages.
International Search Report for PCT/US2009/004307, mailed Nov. 27, 2009, 6 pages.
International Search Report for PCT/US2012/050785, mailed Nov. 23, 2012, 6 pages.
Chinese Search Report in Application No. 200980158768.9, dated Jun. 16, 2013, 4 pages.

* cited by examiner

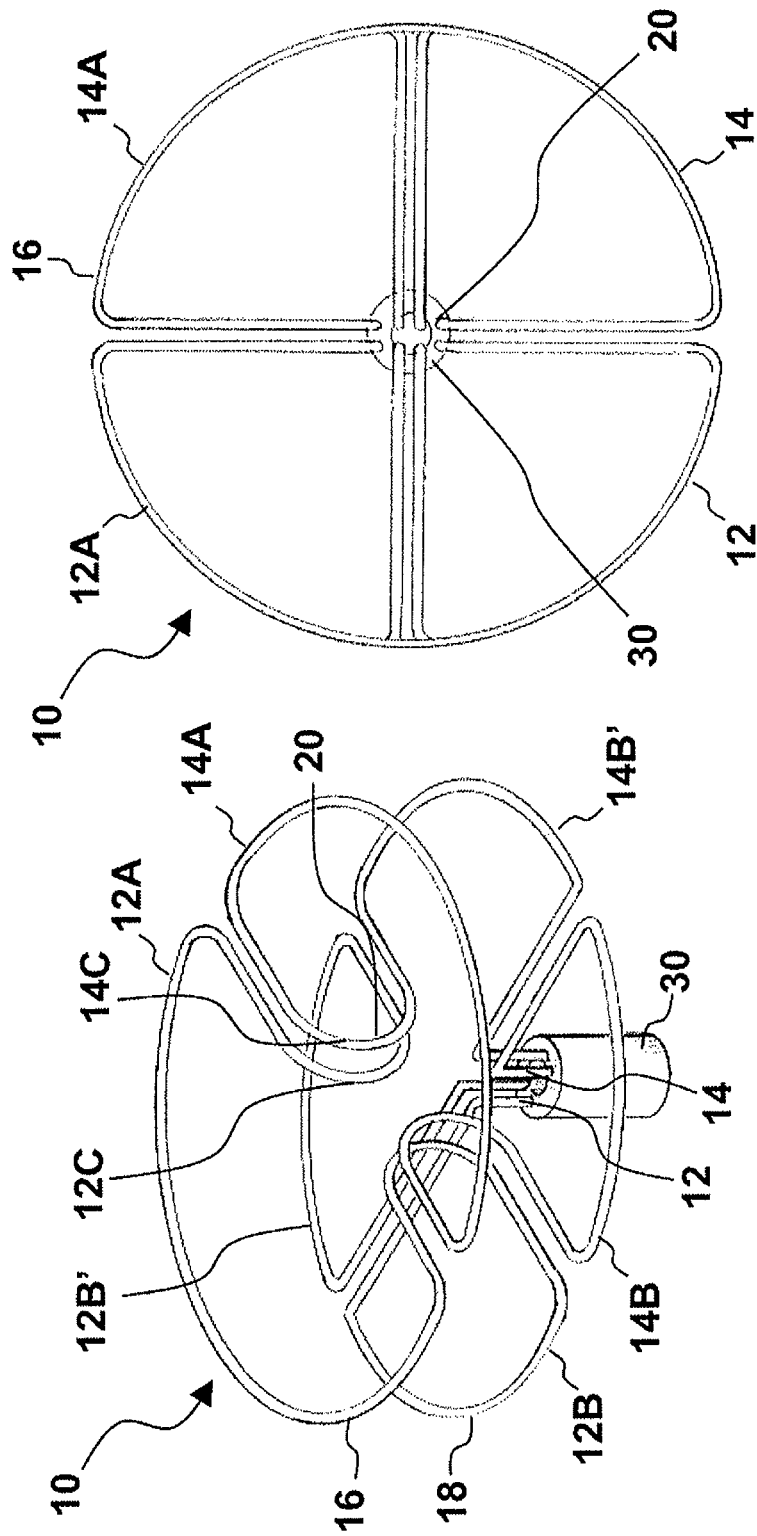

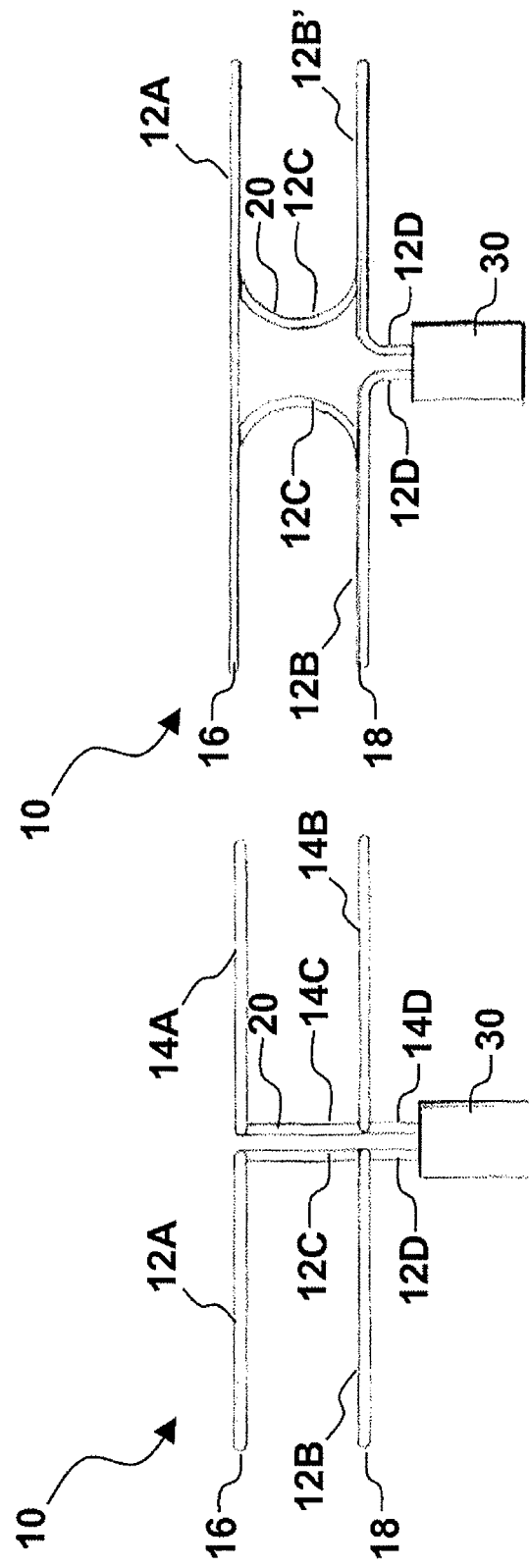

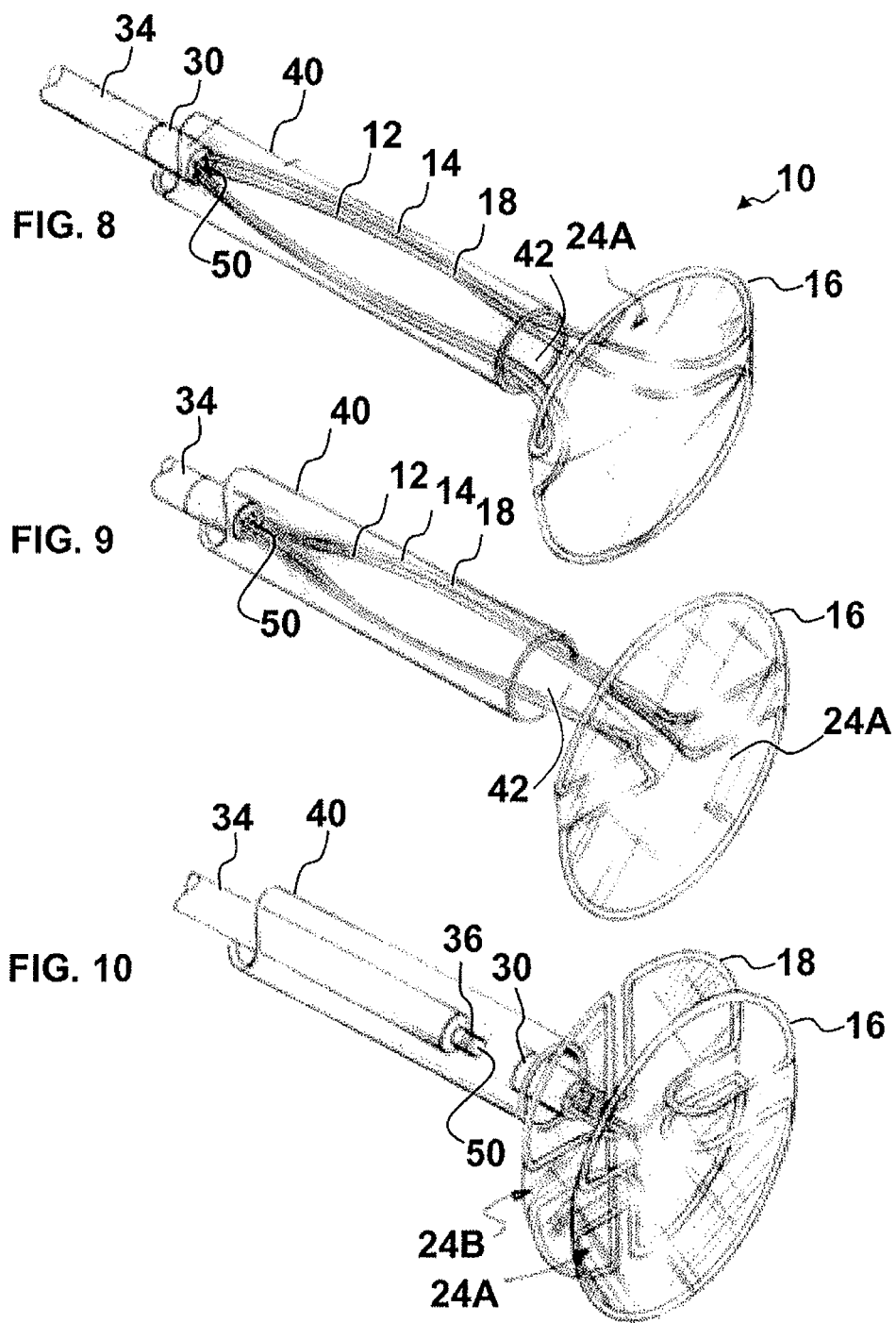

HEART OCCLUSION DEVICES

REFERENCE TO RELATED APPLICATION

The application claims priority to U.S. Provisional Application entitled "HEART OCCLUSION PLUG," Ser. No. 61/034,772, filed Mar. 7, 2008, which is incorporated herein by reference in its entirety.

FIELD OF THE INVENTION

The present invention is directed to a medical device and particularly to a device for closing congenital cardiac defects. The present invention is specifically directed to a heart occlusion device with a self-centering mechanism.

DESCRIPTION OF THE PRIOR ART

Heart occlusion devices for correcting congenital heart defects, such as atrial septal defects ("ASD"), patent foramen ovale ("PFO") defects, ventricular septal defects ("VSD"), and patent ductus arteriosus ("PDA") defects, are known to the medical field. The following companies manufacture different types of devices: AGA Medical, Microvena Corp./EV3 Medical, Velocimed/St. Jude Medical, Occlutech International, NMT Medical, Cardia, Inc., Solysafe SA, Sideris (Custom Medical, Inc.), WL Gore, and Cook, Inc.

A specific example of one such heart defect is a PFO. A PFO, illustrated in FIG. 1 at 6A, is a persistent, one-way, usually flap-like opening in the wall between the right atrium 2 and left atrium 3 of the heart 1. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 2 to the left atrium 3, and blood clots could enter the systemic circulation. It is desirable that this circumstance be eliminated.

The foramen ovale 6A serves a desired purpose when a fetus is gestating in utero. Because blood is oxygenated through the umbilical chord and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 8 and septum secundum 9. However, a PFO has been shown to persist in a number of adults.

The presence of a PFO defect is generally considered to have no therapeutic consequence in otherwise healthy adults. Paradoxical embolism via a PFO defect is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO defect and the risk for paradoxical embolism or stroke. In addition, there is significant evidence that patients with a PFO defect who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO defect. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. The flap-like opening of the PFO is complex, and devices with a central post or devices that are self-centering may not close the defect completely, an outcome that is highly desired when closing a PFO defect. Hence, a device with a waist which can conform to the defect will have much higher chance of completely closing the defect. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Devices for occluding other heart defects, e.g., ASD, VSD, PDA, also have drawbacks. For example, currently available devices tend to be either self-centering or non-self-centering and may not properly conform to the intra-cardiac anatomy. Both of these characteristics have distinct advantages and disadvantages. The non-self centering device may not close the defect completely and may need to be over-sized significantly. This type of device is usually not available for larger defects. Further, the self-centering device, if not sized properly, may cause injury to the heart.

Some have sharp edges, which may damage the heart causing potentially clinical problems.

Some devices contain too much nitinol/metal, which may cause untoward reaction in the patient and hence can be of concern for implanting physicians and patients.

Some currently marketed devices have numerous model numbers (several available sizes), making it difficult and uneconomical for hospitals and markets to invest in starting a congenital and structural heart interventional program.

The present invention is designed to address these and other deficiencies of prior art aperture closure devices.

SUMMARY OF THE INVENTION

The present invention is directed to a heart occlusion device with a self-centering mechanism comprising two separate, uniquely-shaped wires wherein each wire is shaped into two semi-circular designs to form two half-discs by the memory-shaping capability of the wires, a self-centering waist area formed between the two semi-circular designs, and a covering over the each of the two semi-circular designs, wherein the covering is a sealant from the heart occlusion.

More specifically, the present invention is directed to a device for occluding an aperture in tissue comprising a first flexible wire and a second flexible wire, wherein each of the first and second wires is comprised of a shape memory properties, and wherein each of the first and second wires is shaped into first and second generally semi-circular forms such that the first semicircular form of the first wire opposes the first semicircular form of the second wire to form a first disc and the second semicircular form of the first wire opposes the second semicircular form of the second wire to form a second disc wherein further each of the first and second discs is separated by a self-centering waist formed from two sections of the first wire and two sections of the second wire; and a sealed covering over each of the first and second discs, wherein the covering provides a seal to occlude the aperture.

The present invention is also directed to a device for occluding an aperture in a heart tissue comprising a first flexible wire and a second flexible wire. Each of the first and second wires is comprised of a shape memory property. Further, each of the first and second wires is shaped into first and second generally semi-circular forms such that the first semicircular form of the first wire opposes the first semicircular form of the second wire to form a first disc and the second semicircular form of the first wire opposes the second semicircular form of the second wire to form a second disc. Each of the first and second discs is separated by a self-centering waist formed from two sections of the first wire and two sections of the second wire, and wherein the two sections of the first wire and two sections of the second wire create an outward radial force to maintain the self-centering configuration of the device. Each of the first and second wires has a first and second end and wherein each of the first and second ends of the first and second wires is connected to a hub, wherein the hub further comprises a delivery attachment mechanism for attachment to a deployment cable. The device also includes a sealed covering over each of the first and second discs, wherein the covering provides a seal to occlude the aperture wherein the coverings comprise a flexible, biocompatible material capable of promoting tissue growth and/ or act as a sealant.

The present invention is also directed to a method for inserting the occluder device described above into an aperture defect in a heart to prevent the flow of blood therethrough. The method comprises:
 a. attaching the occluder device to a removable deployment cable,
 b. placing the occluding device within a flexible delivery catheter having an open channel,
 c. feeding the catheter into a blood vessel and advancing the catheter via the blood vessel system to the aperture defect in the heart,
 d. advancing the catheter through the aperture defect,
 e. withdrawing the catheter from the occluder device such that the first disc of the occluder device expands on one side of the aperture defect,
 f. further withdrawing the catheter from the occluder device such that the second disc of the occluder device expands of the other side of the aperture defect, such that the waist of the occluder device expands by memory retention within the aperture defect to self-center the occluder device,
 g. further withdrawing the catheter from the blood vessel; and
 h. removing the deployment cable from the hub.

Advantages:
 The device of the present invention has many advantages:
 Lower Profile: The occluder device of the present invention has a lower profile than available devices,
 Conformable: The device is flexible and conformable to the patient anatomy, specifically the hole that is being closed. There are no sharp edges. The device is soft and hence less traumatic to the atrial tissue.
 Self-Centering on Demand: Because of the unique way the two discs are connected, the device has self-centering characteristics. The uniqueness of this device is in the self-centering mechanism. The waist of the device is made of four wires. The wires will have the capability to conform to the shape and size of the defect in the organ—a characteristic not seen in prior art devices. Therefore, the self-centering of the device is dependent upon the size and the shape of the defect. The wires will have enough radial force to maintain the self-centering configuration but will not be strong enough to press against the defect edges in a manner that exacerbates the defect. The device is fully repositionable and retrievable after deployment.
 Custom Fit: The device has the further ability to be custom-fit within the defect with balloon-expansion of the waist. Because of the self-expanding nature of the waist, this will not be needed in most cases. However, in cases in which custom expansion is needed (oval defects, tunnel defects), the waist size can be increased to conform to the defect by the balloon catheter expansion. A balloon may be inserted through a hollow screw attachment on the device's delivery hub and delivery cable. The expansion will be possible before the release of the device, which will increase the margin of safety.
 Fewer Sizes: The expandable waist requires fewer sizes to close a wider variety of differently-sized defects. Thus, a single device may offer physicians the ability to implant devices in several different sizes.
 The device will be less thrombogenic as the discs will be covered with ePTFE. The ePTFE has been time-tested and found to be least thrombogenic. There is the ability to close defects up to 42 mm with very mild modifications.
 Security: There will be the opportunity to remain tethered to the implanted device before releasing it, which is an extra security feature.

Uses:
 The device of the present invention should be appropriate for an ASD (atrial septal defect), PFO (patent foramen ovale), VSD (ventricular septal defect), and PDA (patent ductus arteriosus) with minor modifications.
 An important use of the device will also be in closure of an aperture in a left atrial appendage. The device can be modified to conform to the atrial appendage anatomy. The discs are modified so that the device is not extruded out with the heartbeats. Yet, the device is still soft enough to form adequate closure.
 The discs can also be modified so that they become compatible for closure of veins and arteries. For this use, the connecting waist will become equivalent (or near equivalent) to the diameter of the discs. Other important uses will be in closure of coronary artery fistulas, arteriovenous fistulas, arteriovenous malformations, etc.
 The objects and advantages of the invention will appear more fully from the following detailed description of the

BRIEF DESCRIPTION OF THE DRAWINGS

FIG. 2 is a perspective view of the occluder device of the present invention.

FIG. 3 is a top plan view of the occluder device of FIG. 2.

FIG. 4 is a side plan view of the occluder device taken along lines in FIG. 2.

FIG. 5 is a side plan view of the occluder device taken along in FIG. 2.

FIG. 8 is a perspective view of the occluder device first emerging from the catheter.

FIG. 9 is a perspective view of the occluder device half-way emerged from the catheter.

FIG. 10 is a perspective view of the occluder device fully emerged from the catheter and separated from the deployment cable.

DETAILED DESCRIPTION OF THE INVENTION

The present invention provides a device for occluding an aperture within body tissue. One skilled in the art will recognize that the device and methods of the present invention may be used to treat other anatomical conditions in addition to those specifically discussed herein. As such, the invention should not be considered limited in applicability to any particular anatomical condition.

Figure 1:
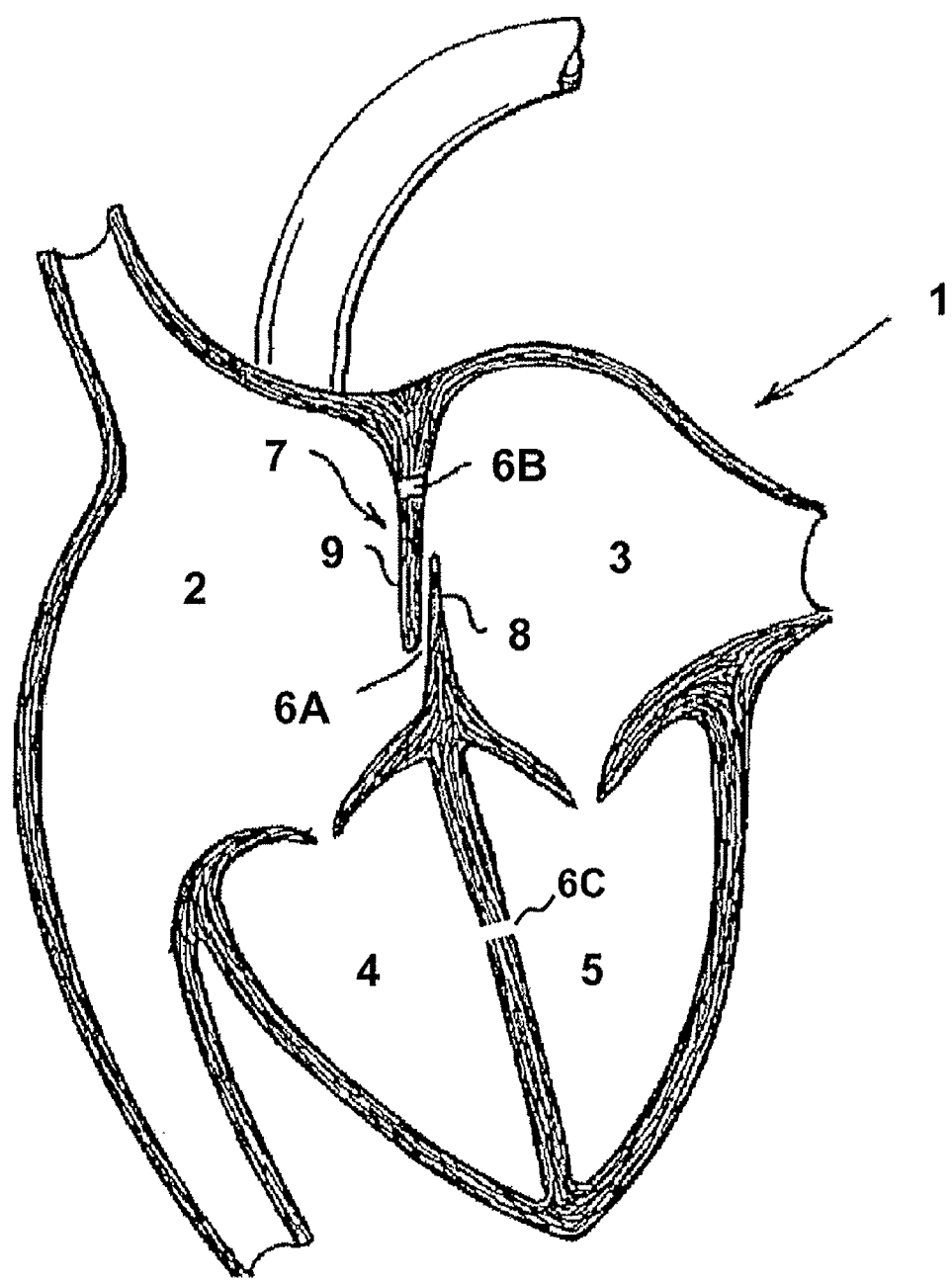
FIG. 1 is a schematic representation of a human heart including various septal defects.

FIG. 1 illustrates a human heart 1, having a right atrium 2, a left atrium 3, a right ventricle 4, and a left ventricle 5. Shown are various anatomical anomalies 6A, 6B, and 6C. The atrial septum 7 includes septum primum 8 and septum secundum 9. The anatomy of the septum 7 varies widely within the population. In some people, the septum primum 8 extends to and overlaps with the septum secundum 9. The septum primum 8 may be quite thin. When a PFO is present, blood could travel through the passage 6A between septum primum 8 and septum secundum 9 (referred to as "the PFO tunnel"). Additionally or alternatively, the presence of an ASD could permit blood to travel through an aperture in the septal tissue, such as that schematically illustrated by aperture 6B. A VSD is similar to an ASD, except that an aperture 6C exists in the septum between the left and right ventricle of the heart.

PDA results from defects in the ductus arteriosus. The human blood circulation comprises a systemic circuit and a pulmonary circuit. In the embryonic phase of human development, the two circuits are joined to one another by the ductus arteriosus. The ductus connects the aorta (circulation to the body) to the pulmonary artery (pulmonary circuit). In normal development of an infant, this ductus closes after birth. If development is defective, it can happen that the ductus does not close, and as a result the two blood circuits are still joined even after birth.

Unless specifically described otherwise, "aperture" 6 will refer to the specific heart defects described above, including PFO 6A, ASD 6B, VSD 6C, and PDA among others.

As used herein, "distal" refers to the direction away from a catheter insertion location and "proximal" refers to the direction nearer the insertion location.

As used herein, "memory" or "shape memory" refers to a property of materials to resume and maintain an intended shape despite being distorted for periods of time, such as during storage or during the process of delivery in vivo.

Referring now to FIGS. 2-5, the occluder device 10 of the present invention comprises two separate uniquely shaped memory wires 12, 14. The wire can be formed of biocompatible metals or polymers, such as bioresorbable polymers, shape memory polymers, shape memory metal alloys, biocompatible metals, bioresorbable metals, or combinations thereof. Specific examples include but are not limited to iron, magnesium, stainless steel, nitinol, or combinations of these and similar materials. A preferred metal for the present invention is a nitinol alloy. Nitinol (an acronym for Nickel Titanium Naval Ordnance Laboratory) is a family of intermetallic materials, which contain a nearly equal mixture of nickel (55 wt. %) and titanium. Other elements can be added to adjust or "tune" the material properties. Nitinol exhibits unique behavior, specifically, a well defined "shape memory" and super elasticity. In general, any biocompatible material with a memory capability can be used with the present invention. The thermal shape memory and/or superelastic properties of shape memory polymers and alloys permit the occluder 10 to resume and maintain its intended shape in vivo despite being distorted during the delivery process. In certain embodiments, the memory may also assist in pressing an aperture, such as a PFO tunnel, closed. The diameter or thickness of the wire depends on the size and type of the device, i.e., the larger the device, the larger the diameter of the wire. In general, wire having a diameter between about 0.2 mm and 0.8 mm can be used.

As shown in FIGS. 2-5, each wire 12 or 14 forms a shape which mirrors that of the respective wire 14 or 12. Specifically, each wire 12, 14 forms a distal semi-circle or half-disc 12A 14A in addition to two proximal quarter-circles or quarter-discs 12B, 12B' or 14B, 14B'. The two proximal quarter-circles of each wire together form proximal semi-circles or half-discs 12B, 12B' or 14B, 14B'. The two distal semi-circles of each respective wire 12A, 14A together comprise a distal circle or distal disc 16 of the occluder 10. The four proximal quarter-circles 12B, 12B', 14B, 14B', which form a "four-leaf clover" configuration, comprise a proximal circle or proximal disc 18 of the occluder 10.

The proximal semi-circle 12B, 12B' or 14B, 14B' of each wire is connected to the distal semi-circle 12A or 14A by waist portions 12C, 14C. As shown in FIG. 2, there are two waist portions 12C, 14C per wire. The four waist portions (two from each wire) 12C, 14C together comprise a restricted area or waist 20 of the occluder device 10. The distance between the waist portions, both within the same wire and from wire to wire, determines the size of the waist 20. The size of the waist 20 is dependent on the particular application and the size of the occluder device 10. The resiliency and memory of the waist portions 12C, 14C and capacity to expand radially serves as a self-centering mechanism of the occluder device 10 in apertures 6.

The Hub 30:

The two half-discs are not attached or joined to each other except at the junction of the delivery attachment mechanism or hub 30. The ends 12D, 14D of wires 12, 14 will be welded or otherwise connected to the hub 30.

Figure 7:
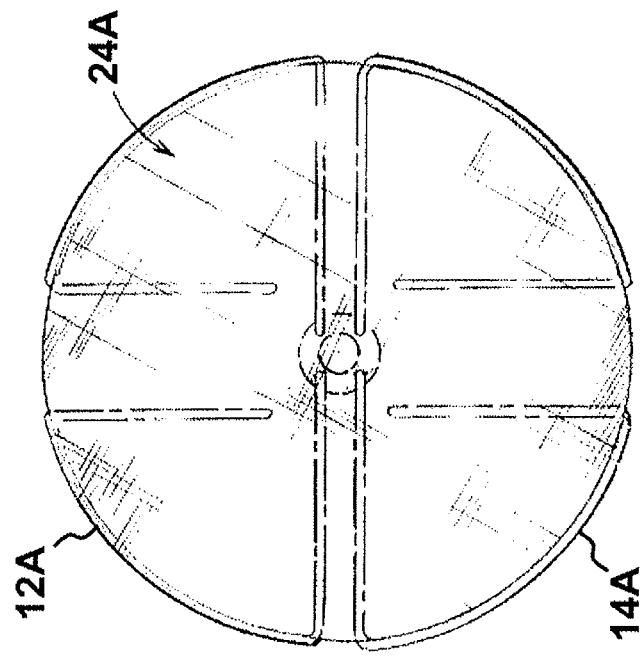
FIG. 7 is a top plan view of the occluder device of FIG. 6.
Figure 6:
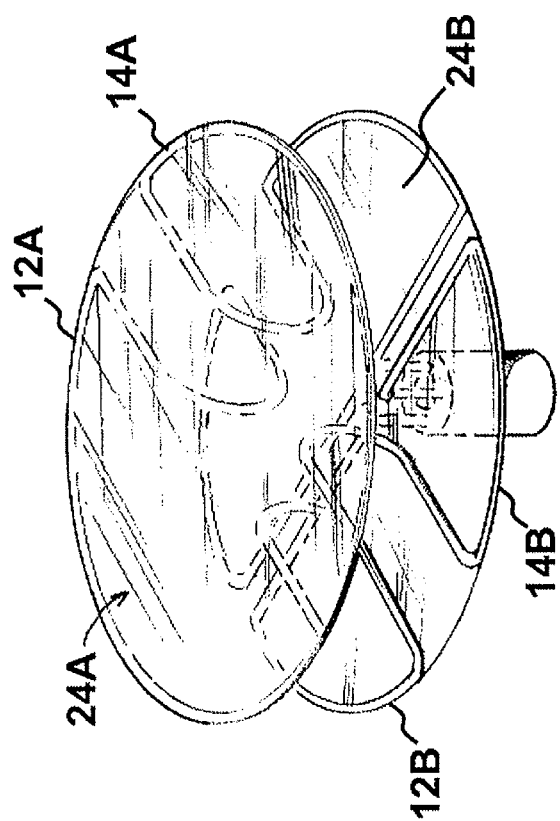
FIG. 6 is a perspective view of the occluder device of FIG. 2, illustrating the covering 42.

Coverings 24A and 24B:

According to some embodiments of the present invention, the distal disc 16 and/or proximal disc 18 may include membranous coverings 24A and 24B illustrated in FIGS. 6 and 7. The membranous coverings 24A and 24B ensure more complete coverage of aperture 6 and promote encapsulation and endothelialization of tissue, thereby further encouraging anatomical closure of the tissue and improving closure rate. The coverings 24A and 24B also help stabilize the occluder device 10.

The membranous coverings 24A and 24B may be formed of any flexible, biocompatible material capable of promoting tissue growth and/or act as a sealant, including but not limited to DACRON®, polyester fabrics, Teflon-based materials, ePTFE, polyurethanes, metallic materials, polyvinyl alcohol (PVA), extracellular matrix (ECM) or other bioengineered materials, synthetic bioabsorbable polymeric materials, other natural materials (e.g. collagen), or combinations of the foregoing materials. For example, the membranous coverings 24A and 24B may be formed of a thin metallic film or foil, e.g. a nitinol film or foil, as described in U.S. Pat. No. 7,335,426 (the entirety of which is incorporated herein by reference). The preferred material is Poly(tetrafluoroethene) (ePTFE) as it combines several important features such as thickness and the ability to stretch. Loops may also be stitched to the membranous coverings 24A and 24B to securely fasten the coverings to occluder 10. The coverings may alternatively be glued, welded or otherwise attached to the occluder 10 via the wires 12, 14.

Size:

As illustrated in FIGS. 2-7, the diameters of the distal disc 16 and proximal disc 18 are generally 5-8 mm larger than the diameter of the connecting waist 20. For example, if the diameter of the connecting waist 20 is 4 mm, the diameters of the discs 16,18 are generally about 9 mm each. Because of the flexibility in the waist 20, a 12 mm waist device will be able to be placed in a 6 mm to 12 mm defect. For larger waists 20 or larger devices, the diameter of the disc size will increase proportionately.

It is within the scope of the present invention to envision occluder devices available in 7 or more sizes, specifically waist size having the following diameters for different-sized apertures 6: 6 mm, 12 mm, 18 mm, 24 mm, 30 mm, 36 mm, and 42 mm.

Operation:

In general, the occluder 10 may be inserted into an aperture 6 to prevent the flow of blood therethrough. As a non-limiting example, the occluder 10 may extend through a PFO 6A or an ASD 6B such that the distal disc 16 is located in the left atrium 3 and the proximal disc 18 is located in the right atrium 2 (as shown in the heart 1 in FIG. 1). The closure of apertures in these and other tissues, as well as other types of apertures, will become apparent as described below.

Referring now to FIGS. 8-10, the occluder device 10 is attached to a deployment cable 34 which is removably attached to the occluder device 10 at the hub 30. As illustrated in FIG. 10, one method of releasably attaching the deployment cable 34 to the hub 30 is by threaded engagement utilizing a screw end 36 which engages unseen female threads within the hub 30. Other known means of attachment can be used to releasably connect the deployment cable 34 to the hub 30.

When the deployment cable 34 is engaged with the hub 30, as illustrated in FIGS. 8 and 9, the occluder device 10 is initially housed within a flexible delivery catheter 40 having an open channel 42. Reference is made to FIG. 8 which illustrates the occluder device 10 in which the distal disc 16 is expanded, due to the memory expansion of the wires 12 and 14, and housed within the open channel 42 of the delivery catheter 40. During the initial stages of placement of the occluder device 10, both the distal disc 16 and proximal disc 18 as well as the coverings 24A and 24B are housed within the open channel 42 of the delivery catheter 40. In this manner, the catheter 40 is fed into the blood vessel through an already placed sheath and advanced via the blood vessel system to a defect in the heart Once the delivery catheter 40 traverses the aperture that needs to be occluded, e.g., a hole in the heart, the device 10 will be partially advanced from the catheter 40 as illustrated in FIG. 8. As the device 10 leaves the catheter 40, the distal disc 16, which includes the covering 24A, begins to expand on the distal side of the aperture. Due to the memory capabilities of the wires 12 and 14, the occluder device 10 begins to return to its normal shape such that the distal disc 16 expands on distal side of the aperture in the heart. Once the distal disc 16 is completely out of the catheter opening 42, as show in FIG. 9, it 16 and the attached covering 24A become fully expanded. The catheter 40 is further withdrawn to expose the waist 20 which then begins to emerge and expand due to the memory shape of the wires 12 and 14. Advantageously, the waist 20 is designed to expand such that each of the wires forming the waist 20 are urged against the aperture in the heart causing a custom fit device of the occluder 10 within the aperture. As the catheter 40 is further withdrawn, the proximal disc 18 and the covering 24B begin their process of expansion on the proximal side of the aperture. When the proximal disc 18 is fully delivered from the catheter 40, it will expand and effectively form a seal over the aperture. The distal disc 16 and proximal disc 18 are secured in place by the action of the wires in the waist 20 urging against the aperture. At this stage, as shown in FIG. 10, the deployment cable 34 is removed from the hub 30 and the catheter 40 and the deployment cable 34 are removed from the body. The occluder device 10 is left in the heart at the region of the aperture. Over several months, skin tissue and other membranous structures will bind to the occluder device 10 thereby permanently locking the occluder device 10 to the specific area in the heart.

The two wires 12, 14 function to form round discs 16, 18 on each side of the tissue. The discs 16, 18 maintain the circular shape because of the memory capability of the wires 12, 14. The coverings 24A, 24B will stabilize the discs and will act to completely occlude the defect.

The wires 12, 14 at the waist portions 12C, 14C will be separated enough at the waist 20 to make the occluder device 10 self-centering. Due to the conformity of this design, the occluder device 10 should self-center within commonly (round, oval) shaped septal defects as the waist 20 can adjust to any type of opening.

If a larger-diameter waist 20 is required, the waist 20 has the capability to expand (only if needed) to a larger size with the help of a balloon. In this manner, a center channel 50 extends through the deployment cable 34, the hub 30, and the screw end 36. A balloon (not shown) is urged through the center channel 50 after the occluder device has been removed from the catheter 40 and expanded. The balloon is placed within the waist 20 and expanded. The waist 20 is dilatable, i.e., expandable, when gentle pressure of the balloon is applied. The dilation will expand the waist portions 12C, 14C. Once the desired diameter is reached, the balloon is deflated and removed by withdrawal through the center channel 50. Once the occluder device 10 appears stable, the device 10 is separated from the deployment cable 34 as discussed above. In the majority of cases, balloon dilation will not be required.

Figure 11:
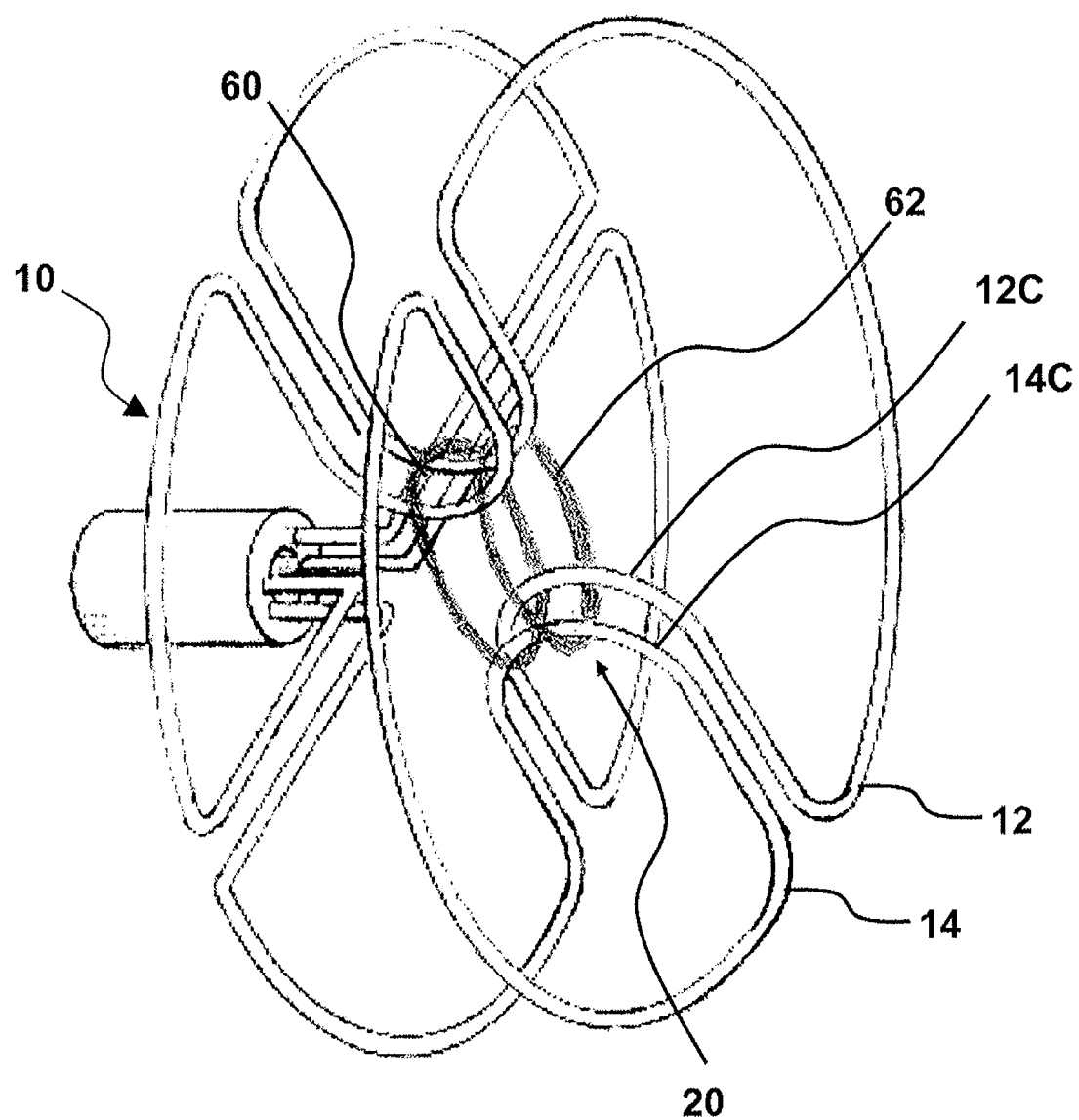
FIG. 11 is a perspective view of the occluder device of the present invention illustrating restriction wires encircling the waist of the occluder device.

Restriction Wires 6, 62 (FIG. 11):

In order to increase stability in the occluder device 10 and to avoid significant crimping of the waist 20 or the proximal or distal discs 18, 16, the waist 20 can be encircled by one or more restriction wires 60, 62 as illustrated in FIG. 11. The restriction wires 60, 62 can be made of the same wire material as the wires 12 and 14, or the may be of a different material, such as plastic wire, fish line, etc. The restriction wires 60, 62 may be welded or otherwise connected to the waist portions 12C, 14C. The purpose of the restriction wires 60 or 62 is also to restrict the circumference of the waist 20 if necessary. Although one restriction wire 60 is generally suitable, a second restriction wire 62 can also be incorporated to further improve stability.

Alternative Embodiments

Reference is now made to FIGS. 12-15 for alternative embodiments of the occluder device 10 of the present invention. Unless otherwise noted, the same reference numbers will be applied to similar structures in each embodiment.

Figure 12A:
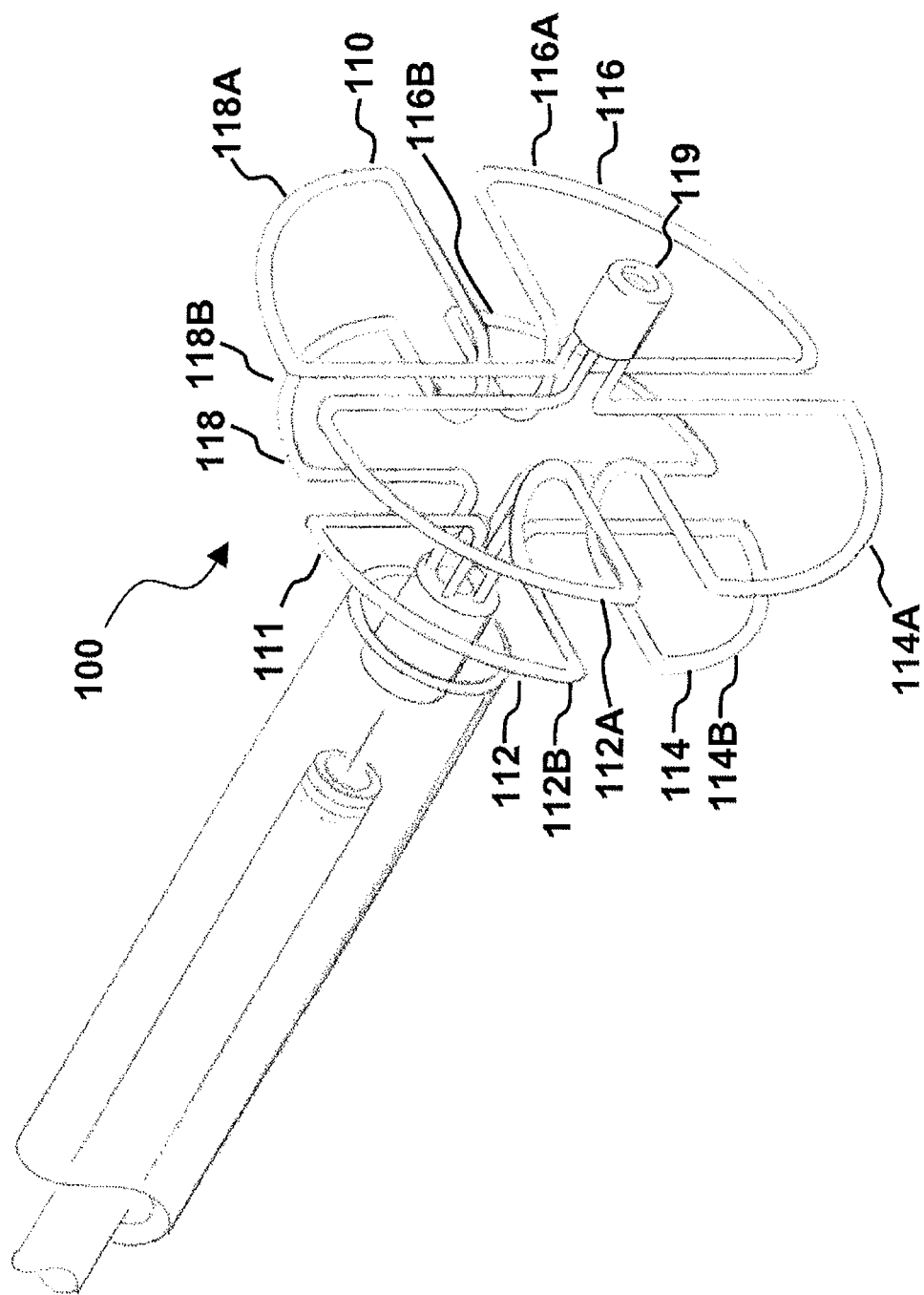
FIG. 12A is a perspective view of a first alternative embodiment of the occluder device of the present invention.
Figure 12B:
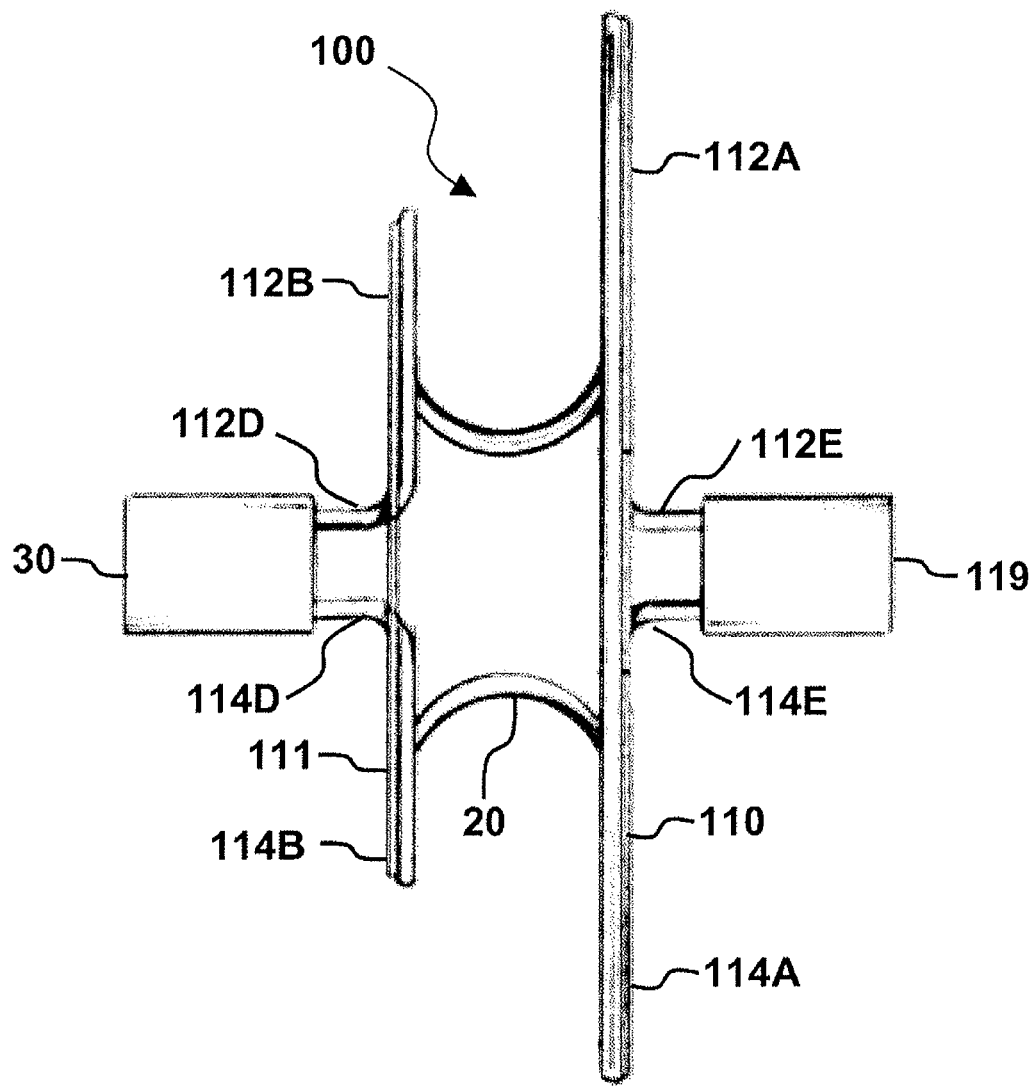
FIG. 12B is a side plan view of the first alternative embodiment of the occluder device of the present invention as shown in FIG. 12A.

Reference is made to FIGS. 12A and 12B for an alternative embodiment of the occluder device 100. The occluder device 100 in this embodiment is designed for PDA procedures. This embodiment is similar to previously described embodiments except that it is comprised of four wires 112, 114, 116, 118 rather than two wires. In this case, each wire forms a mirror image of each of its neighboring wires. For example, wire 112 mirrors wire 114 as well as wire 118, etc. Each of the four wires 112, 114, 116, 118 forms a proximal quarter-disc 112B, 114B, 116B, 118B and a distal quarter-disc 112A, 114A, 116A, 118A. The proximal quarter-discs 112B, 114B, 116B, 118B together form a proximal disc 111 in a "four-leaf clover" configuration, and the distal quarter-discs 112A, 114A, 116A, 118A together form a distal disc 110 also in a "four-leaf clover" configuration. This embodiment also differs from previously-described embodiments in that the waist 20 is comprised of a single portion of each of the four wires 112, 114, 116, 118. This embodiment further differs from previously-described embodiments in that it comprises a second hub 119 with a screw mechanism. The second hub 119 connects to the distal disc 110 by distal ends 112E, 114E (116E, 118E behind 112E, 114E in FIG. 12B) of each of the four wires 112, 114, 116, 118, just as proximal ends 112D, 114D (116D, 118D behind 112D, 114D in FIG. 12B) connect to the proximal hub 30. The wires 112, 114, 116, 118 may be connected to the hubs 30, 119 by welding or other means known in the art. The length of the waist 20 will be anywhere from 4-8 mm. In addition, the distal disc 110 is typically 4-8 mm larger than the waist 20. However, the proximal disc 111 is generally 1-3 mm, preferably 2 mm, larger than the waist 20 diameter. Hence, the diameter of the distal disc 110 is larger than the diameter of the proximal disc 111.

Figure 13:
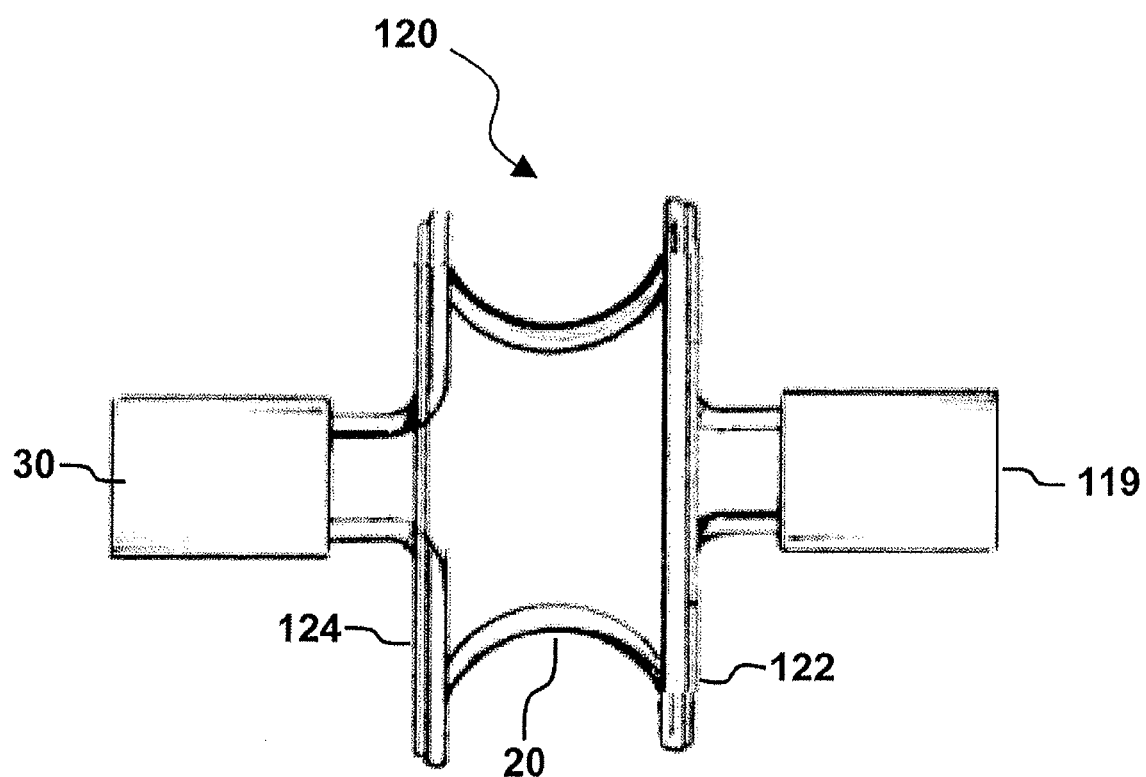
FIG. 13 is a side plan view of a second alternative embodiment of the occluder device of the present invention.

Reference is now made to FIG. 13 for a second alternative embodiment of the occluder device 120. This embodiment, like the embodiment shown in FIGS. 12A and 12B, uses four wires 112, 114, 116, 118 and two hubs 30, 119. It is designed to close apertures in large arteries and veins. In occluder device 120, the distal and proximal discs 122 and 124 are modified so that they are compatible with closure of veins and arteries. For this use, the connecting waist 20 is equivalent or near equivalent to the diameter of each of the discs 122, 124. The diameter of the waist 20 will be 1 mm smaller than the discs 122, 124. The length of the waist will be 4-8 mm. This embodiment can be used in the closure of coronary artery fistulas, arteriovenous fistulas, and arteriovenous malformations.

Figure 14:
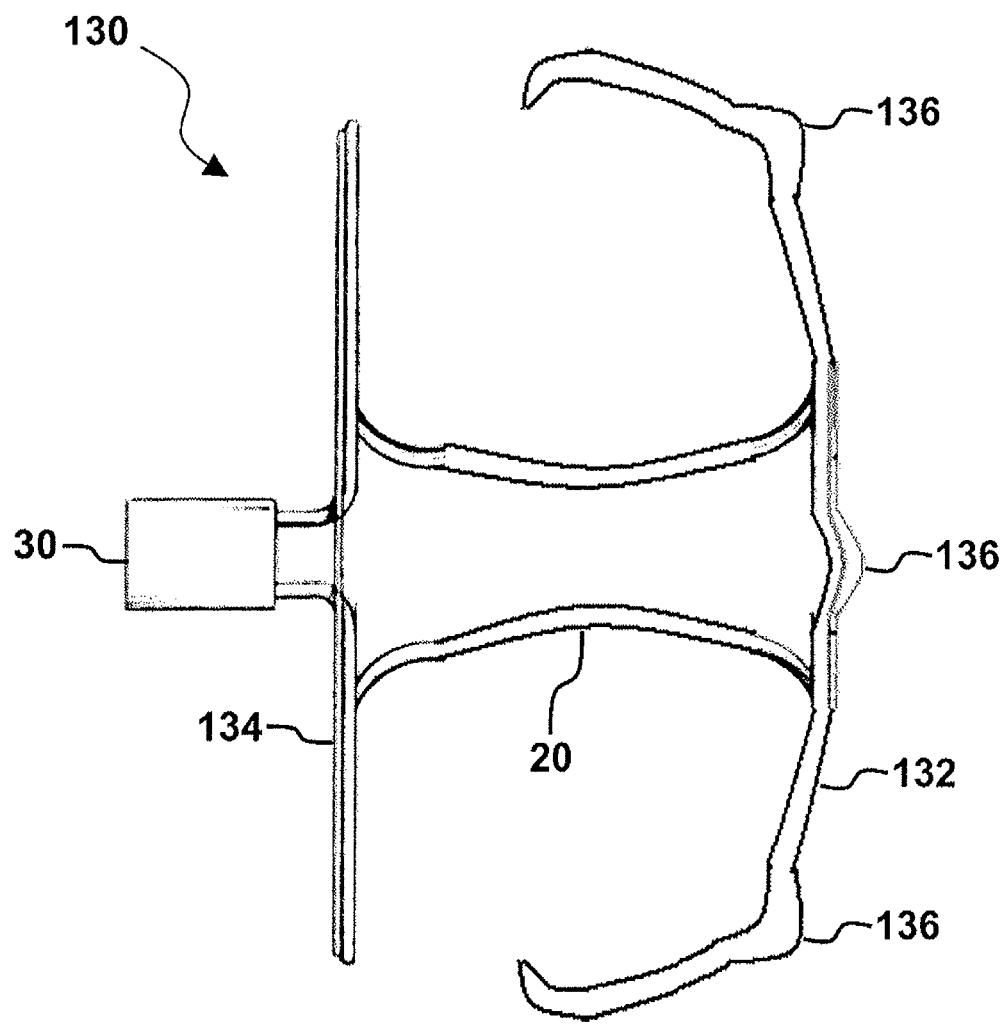
FIG. 14 is a side plan view of a third alternative embodiment of the occluder device of the present invention.

Reference is made to FIG. 14 for a third alternative embodiment of the occluder device 130. The importance of the occluder device 130 will be in the closure of the left atrial appendage. The device 130 is modified to conform to the atrial appendage anatomy. The distal disc 132 is modified so that the device 130 is not extruded out with the heartbeats. For the left atrial appendage occluder device 130, the memory wire structure of the distal disc 132 is woven to form anywhere from 2 to 8 protuberances or hooks 136. Upon inserting the device 10 in an aperture in the left atrial appendage of the heart, the hooks 136 grip the outer portion of the left atrium heart tissue and thereby assist in keeping the device 130 from extruding out of the left atrial appendage with contraction of the heart. The proximal disc 134 is typically flat and similar to the disc formed by the proximal discs 18 in FIGS. 2-7. The proximal disc 134 abuts the inner atrial wall of the heart. Typically, the waist 20 will be about 4-8 mm in diameter. The length of the waist may range from 4 to 16 mm.

Figure 15:
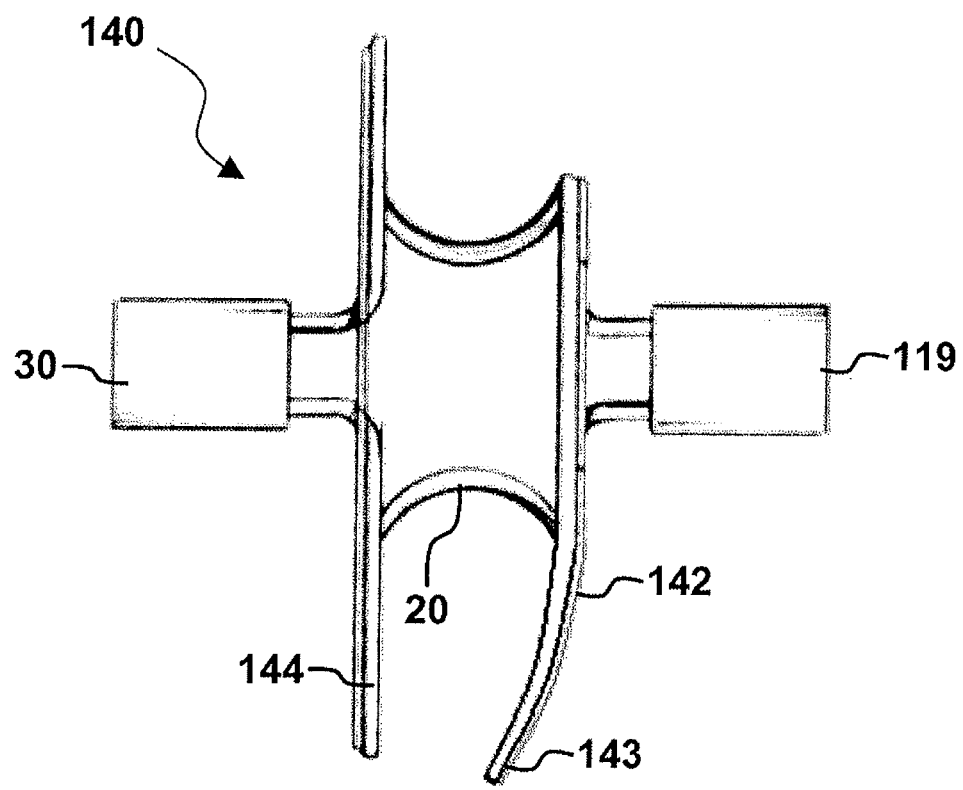
FIG. 15 is a side plan view of a fourth alternative embodiment of the occluder device of the present invention.

Reference is made to FIG. 15 for a fourth alternative embodiment of the occluder device 140. Occluder device 140 is intended occlude perimembranous ventricular septal ("PVS") defects. This embodiment, like the embodiment shown in FIGS. 12A and 12B, uses four wires 112, 114, 116, 118 and two hubs 30, 119. The occluder device 140 is different from other embodiments in that two of the four wires form truncated distal-quarter discs, with the effect that the distal disc 142 substantially misses half of the disc. Therefore, the device 140 has approximately 1.5 discs as opposed to two discs. The half distal disc 142 is also significantly longer than the proximal disc 144. Typically, the distal disc 142 will be 6-8 mm in diameter. In addition, the distal disc 142 converges or curves inwards at 143, i.e., it is angled to contact the ventricular septum when the device 140 is inserted in the PVS defect. (See below for details.) The lower edge of the proximal disc (opposite to the long distal disc) will be 3-4 mm larger than the waist and the other half of the proximal disc will be 2-3 mm larger than the waist. The discs can also be modified to be of different shapes in the same device. Alternatively, the disc angle may be created by a straight distal disc 142 angled with respect to the plane perpendicular to the waist 20 in a slant fashion.

Other embodiments may comprise any combinations of the embodiments described explicitly herein. It is understood that the invention is not confined to the particular construction and arrangement of parts herein illustrated and described, but embraces such modified forms thereof as come within the scope of the following claims.

What is claimed is:

1. A device for occluding an aperture in tissue comprising:
   a. a first flexible wire and a second flexible wire, wherein each of the first and second wires is comprised of memory wire having a shape memory property, and wherein each of the first and second wires is shaped into a half-disc and a generally semi-circular form, such that the half-disc of the first wire opposes the half-disc of the second wire to form a first disc and the semicircular form of the first wire opposes the semicircular form of the second wire to form a second disc, wherein further each of the first and second discs is separated by a waist that configures the device to be self-centering, the waist comprised of two sections of the first wire and two sections of the second wire; and b. a sealed covering over each of the first and second discs, wherein the covering provides a seal to occlude the aperture.

2. The device of claim 1, wherein the two sections of the first wire and two sections of the second wire are configured to create an outward radial force to maintain the self-centering configuration of the device.

3. The device of claim 1 wherein the memory wire comprises a material selected from the group consisting of biocompatible metals or polymers, bioresorbable polymers, shape memory polymers, shape memory metal alloys, biocompatible metals, bioresorbable metals, and combinations thereof.

4. The device of claim 1 wherein the memory wire comprises a material selected from the group consisting of iron, magnesium, stainless steel, nitinol, and combinations of these and similar materials.

5. The device of claim 1 wherein the memory wire is a nitinol alloy.

6. The device of claim 1 wherein each of the first and second wires has a first and second end and wherein each of the first and second ends of the first and second wires are connected to a hub, wherein the hub further comprises a delivery attachment mechanism for attachment to a deployment cable.

7. The device of claim 6 designed for patent ductus arteriosus procedures, wherein a. the length of the waist is approximately 4-8 mm; b. the first disc is approximately 4-8 mm larger than the waist; and c. the second disc is approximately 1-3 mm larger than the waist; and wherein further the device comprises a second opposing hub.

8. The device of claim 6 designed for closing apertures in blood vessels, wherein a length of the waist is substantially equivalent to a diameter of the first disc and to a diameter of the second disc.

9. The device of claim 6 designed for closing perimembranous ventricular septal defects, wherein the first disc is semicircular in shape and wherein the first disc is generally larger than the second disc, and wherein further the device comprises a second opposing hub.

10. The device of claim 1 wherein the covering comprises, a flexible, biocompatible material capable of promoting tissue growth, acting as a sealant, or promoting tissue growth and acting as a sealant.

11. The device of claim 1 wherein the covering comprises materials selected from the group consisting of DACRON, polyester fabrics, TEFLON-based materials, ePTFE, polyurethanes, metallic materials, polyvinyl alcohol, extracellular matrix, bioengineered materials, synthetic bioabsorbable polymeric materials, collagen, and combinations of the foregoing materials.

12. A device for occluding an aperture in tissue comprising:

a. a first flexible wire and a second flexible wire, wherein each of the first and second wires is comprised of memory wire having a shape memory property, and wherein each of the first and second wires is shaped into a half-disc and a generally semi-circular form, such that the half-disc of the first wire opposes the half-disc of the second wire to form a first disc and the semicircular form of the first wire opposes the semicircular form of the second wire to form a second disc, wherein further each of the first and second discs is separated by a waist that configures the device to be self-centering, the waist comprised of two sections of the first wire and two sections of the second wire, and further including at least one restriction wire surrounding the waist; and b. a sealed covering over each of the first and second discs, wherein the covering provides a seal to occlude the aperture.

13. The device of claim 12 wherein the two sections of the first wire and two sections of the second wire are configured to create an outward radial force to maintain the self-centering configuration of the device.

14. The device of claim 12 wherein the memory wire comprises a material selected from the group consisting of biocompatible metals or polymers, bioresorbable polymers, shape memory polymers, shape memory metal alloys, biocompatible metals, bioresorbable metals, and combinations thereof.

15. The device of claim 12 wherein the memory wire comprises a material selected from the group consisting of iron, magnesium, stainless steel, nitinol, and combinations of these and similar materials.

16. The device of claim 12 wherein the memory wire comprises a nitinol alloy.

17. The device of claim 12 wherein each of the first and second wires has a first and second end and wherein each of the first and second ends of the first and second wires are connected to a hub, wherein the hub further comprises a delivery attachment mechanism for attachment to a deployment cable.

18. The device of claim 12 wherein the covering comprises a flexible, biocompatible material capable of promoting tissue growth, acting as a sealant, or both promoting tissue growth and acting as a sealant.

19. The device of claim 12 wherein the covering comprises materials selected from the group consisting of DACRON, polyester fabrics, TEFLON-based materials, ePTFE, polyurethanes, metallic materials, polyvinyl alcohol, extracellular matrix, bioengineered materials, synthetic bioabsorbable polymeric materials, collagen, and combinations of the foregoing materials.

20. A device for occluding an aperture in tissue comprising:

a. a first flexible wire and a second flexible wire, wherein each of the first and second wires is comprised of memory wire having a shape memory property, and wherein each of the first and second wires is shaped into a half-disc and a generally semi-circular form, such that the half-disc of the first wire opposes the half-disc of the second wire to form a first disc and the semicircular form of the first wire opposes the semicircular form of the second wire to form a second disc, wherein the first and second discs are separated by a waist that configures the device to be self-centering the waist comprised of two sections of the first wire and two sections of the second wire, wherein further the two sections of the first wire and two sections of the second wire are configured to create an outward radial force to maintain the self-centering configuration of the device; and b. a sealed covering over each of the first and second discs, wherein the covering provides a seal to occlude the aperture.

21. The device of claim 20 wherein the memory wire comprises a material selected from the group consisting of biocompatible metals or polymers, bioresorbable polymers, shape memory polymers, shape memory metal alloys, biocompatible metals, bioresorbable metals, and combinations thereof.

22. The device of claim 20 wherein the memory wire comprises a material selected from the group consisting of iron, magnesium, stainless steel, nitinol, and combinations of these and similar materials.

23. The device of claim 20 wherein the memory wire is a nitinol alloy.

* * * * *

UNITED STATES PATENT AND TRADEMARK OFFICE
CERTIFICATE OF CORRECTION

| | | |
|---|---|---|
| PATENT NO. | : 9,119,607 B2 | Page 1 of 1 |
| APPLICATION NO. | : 12/400445 | |
| DATED | : September 1, 2015 | |
| INVENTOR(S) | : Amin | |

It is certified that error appears in the above-identified patent and that said Letters Patent is hereby corrected as shown below:

In the claims

Column 11, Line 42, claim 10, delete "comprises," and insert -- comprises --

Column 12, Line 53, claim 20, delete "self-centering" and insert -- self-centering, --

Signed and Sealed this
Nineteenth Day of January, 2016

Michelle K. Lee
*Director of the United States Patent and Trademark Office*